United States Patent [19]
Kaiser

[11] Patent Number: 5,597,534
[45] Date of Patent: Jan. 28, 1997

[54] APPARATUS FOR WIRELESS CHEMICAL SENSING

[75] Inventor: Ulrich Kaiser, Warstein, Germany

[73] Assignee: Texas Instruments Deutschland GmbH, Germany

[21] Appl. No.: 283,962

[22] Filed: Jul. 5, 1994

[51] Int. Cl.⁶ ..................................................... G01N 27/07
[52] U.S. Cl. ..................................... 422/82.02; 422/82.01; 340/505
[58] Field of Search ............................ 422/82.01, 82.02, 422/98; 436/163, 150; 340/501, 505

[56] References Cited

U.S. PATENT DOCUMENTS

| | | | |
|---|---|---|---|
| 3,635,564 | 1/1972 | Zuckerman et al. | 356/128 |
| 3,652,223 | 3/1972 | Ludvik | 324/30 X |
| 4,160,971 | 7/1979 | Jones et al. | 340/505 X |
| 4,333,072 | 6/1982 | Beigel | 340/825 |
| 5,041,826 | 8/1991 | Milheiser | 340/825 |
| 5,053,774 | 10/1991 | Schuermann et al. | 342/44 |
| 5,268,683 | 12/1993 | Stolarczyk | 340/854.4 |

*Primary Examiner*—Jeffrey Snay
*Attorney, Agent, or Firm*—Brian C. McCormack; James C. Kesterson; Richard L. Donaldson

[57] ABSTRACT

A method and apparatus for wireless sensing of chemical parameters is provided in which an interrogation unit (14) transmits interrogation signals. A chemical sensor (12) generates an output based on predetermined chemical parameters. The chemical sensor output is measured by a measurement circuit (10). A responder unit (16), which is powered by the interrogation signals, transmits responses to interrogation signals based on the measured data.

14 Claims, 3 Drawing Sheets

APPARATUS FOR WIRELESS CHEMICAL SENSING

TECHNICAL FIELD OF THE INVENTION

This invention relates in general to the field of electronic devices, and more particularly to a method and apparatus for wireless chemical sensing.

CROSS-REFERENCE TO RELATED PATENTS

The following commonly assigned patent applications are hereby incorporated herein by reference:

| Pat No. | Issue Date | TI Case No. |
|---------|------------|-------------|
| 5,053,774 | 10/1/91 | TI-12797A |

BACKGROUND OF THE INVENTION

Chemical sensors are used in a wide variety of applications involving the measurement of various parameters in chemical environments. These measurements are used both in the laboratory and for on-line process control. For example, chemical sensors may be used to measure pH levels or conductivity of chemicals. Normally, these sensors and the related measurement and data acquisition equipment are proximately located and connected by wiring. Often, however, this equipment is placed in locations that have aggressive chemical environments. As a result, measurement and acquisition of data may be difficult and tends to be inaccurate. In addition, it may be expensive to locate data acquisition equipment at every sensor. Therefore, it is frequently necessary to multiplex acquisition equipment among multiple sensors.

Another source of problems with present chemical sensor systems is the wiring itself. Noise may be introduced into the measurement system due to noise induction in the wiring between the sensors, measurement circuits, and data acquisition equipment. In addition, the use of wiring tends to result in no galvanic separation, which may cause ground loops or isolation problems.

Another problem results when attempting to build chemical measurement systems in which data acquisition equipment is multiplexed between multiple sensors. Such systems require data acquisition equipment to be physically moved between different sensors to effectively multiplex the equipment. This results in an inconvenience to the user of the chemical measurement system. Furthermore, additional problems may occur due to the need to constantly detach and reattach data acquisition equipment to different sensors.

SUMMARY OF THE INVENTION

Therefore, a need has arisen to provide a low-cost chemical sensor and related measurement circuit that eliminate wiring in an aggressive chemical environment and permit multiplexing of data acquisition equipment. Specifically, a need has arisen for a wireless chemical sensor that operates without batteries and is addressable.

Furthermore, a need has arisen to operate multiple sensors that permit individual addressing by a single piece of data acquisition equipment.

In accordance with the present invention, a method and apparatus for wireless chemical sensing are provided that substantially eliminate or reduce disadvantages and problems associated with prior chemical sensor systems. In particular, a chemical sensor system for monitoring predetermined parameters is provided. An interrogation unit operates to transmit interrogation signals and receive responses. A chemical sensor is disposed within a chemical environment and generates an output based on the predetermined parameters. In addition, a measurement circuit is associated with each chemical sensor to measure the output of the chemical sensor and provide measurement data. Furthermore, a responder unit, which is powered from the interrogation signals, transmits the measurement circuit data to the interrogation unit.

A particular application for the chemical sensor system involves the use of a plurality of sensors. A single interrogation unit is operable to transmit interrogation signals and receive responses from the plurality of sensors. Furthermore, the interrogation unit is operable to transmit interrogation signals with at least some of the interrogation signals including individual addresses. Each of the responder units has a demodulator for demodulating the interrogation signals into addresses, and a processor for comparing demodulated addresses with the responder unit address. Enabling circuitry is provided in each responder unit to enable the unit to respond only when the demodulated address matches the responder unit address. Therefore, a plurality of chemical sensors, each associated with a separate measurement circuit, can respond to a single interrogation unit.

According to another aspect of the present invention, a method for sensing chemicals and measuring chemical parameters is provided. The method includes the step of transmitting an interrogation signal from an interrogation unit to a responder unit. The responder unit is associated with a chemical sensor and a measurement circuit. The responder unit receives the interrogation signal and provides the responder unit with power. The sensor senses the predetermined characteristic data and the measurement circuit converts the data to measurement data. Data from the measurement circuit are transmitted to the interrogation unit in response to the interrogation signal.

An important technical advantage of the present invention is the fact that the wireless chemical sensor can perform chemical sensing and measurement conveniently and inexpensively. In particular, the sensors are associated with responder units that do not require a local battery or other power supply. Instead, the responder units are powered from interrogation signals received from the interrogation unit.

Furthermore, another important aspect of the present invention is the ability to eliminate wire connections between a chemical sensor, a measurement circuit, and data acquisition equipment. By eliminating wire connections, significant reductions in noise interference are obtained. In addition, another advantage exists in the ability to multiplex data acquisition equipment by supplying each responder unit with an individual address.

BRIEF DESCRIPTION OF THE DRAWINGS

For a more complete understanding of the present invention and the advantages thereof, reference is now made to the following description taken in conjunction with the accompanying drawings in which like reference numbers indicate like features and wherein.

DETAILED DESCRIPTION OF THE INVENTION

Preferred embodiments of the present invention are illustrated in the FIGURES, like numerals being used to refer to like and corresponding parts of the various drawings.

Figure 1:
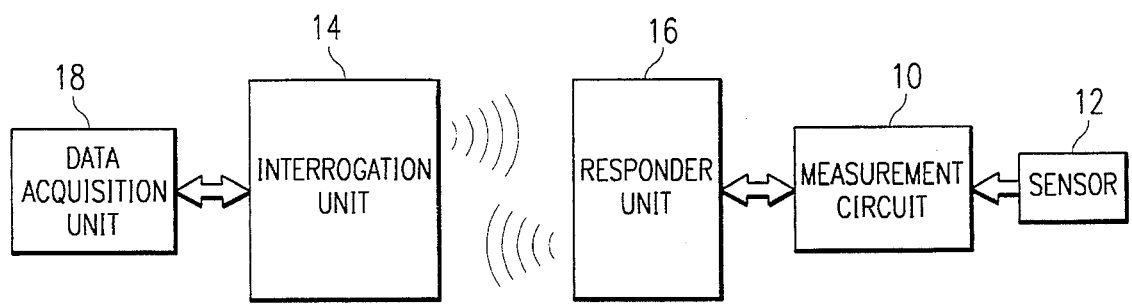
FIG. 1 is a block diagram illustrating a wireless chemical sensor system according to the teachings of the present invention.

FIG. 1 illustrates a chemical sensor system according to the present invention. As illustrated in FIG. 1, a chemical sensor 12 is coupled to a measurement circuit 10. Data from the sensor 12 is provided to the measurement circuit 10. According to one embodiment of the present invention, the chemical sensor 12 measures pH levels. In another embodiment of the invention, the chemical sensor 12 measures conductivity. It should be understood that pH level detection and conductivity detection are presented solely as exemplary embodiments to teach the advantages of the present invention. In addition, the present invention may use other forms of sensors not limited to those previously discussed. The type of chemical sensor 12 used will depend on the particular chemical environment in which the present invention is used.

The measurement circuit 10 is coupled to a responder unit 16. In the present invention, either the raw data from the sensor 12 or processed data from the measurement circuit 10 may be supplied to responder unit 16. As will be discussed below, data is transmitted from the responder unit 16 to an interrogation unit 14. The interrogation unit 14 receives the measurement data from responder unit 16 and either processes and stores the data locally or provides this data to a data acquisition unit 18.

Figure 2A:
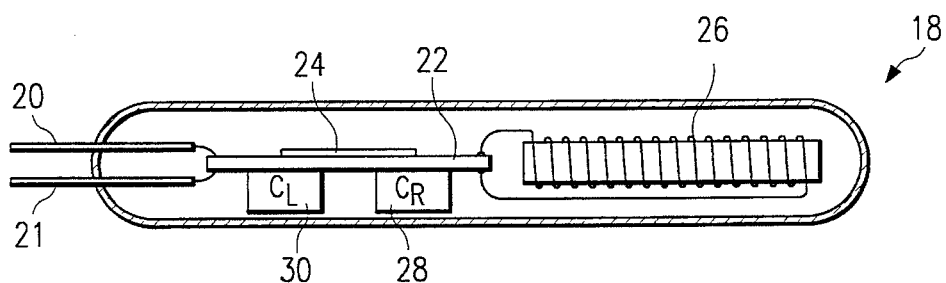
FIG. 2A is a diagram of the integration of a chemical sensor with a measurement circuit and responder unit in a housing according to the teachings of the present invention.

FIG. 2A illustrates a particular embodiment of the responder unit 16, measurement circuit 10, and sensor 12. A housing 18 is provided to contain the chemical sensor system. Such a housing provides an important technical advantage of the present invention, since chemical sensors are often placed in aggressive or hostile environments. In these environments, the measurement circuit 10 and responder unit 16 could potentially be damaged. Therefore, the housing 18 prevents corrosion and other adverse effects upon the chemical sensor system. In a particular embodiment of the present invention, the housing 18 is comprised of glass. However, it should be understood that the use of glass is exemplary only, and other materials that protect the chemical sensor system may also be used for the housing without departing from the intended scope of the present invention.

The sensor 12, comprised of a sensor electrode 20 and a reference electrode 21, extends from housing 18 to permit measurement of predetermined parameters in the chemical environment. In one particular embodiment for measuring pH levels, the sensor electrode 20 is typically a glass electrode. A glass electrode is advantageous because it is not influenced by oxidants or reductants in solutions. A reference electrode 21 completes the circuit and is typically comprised of a mercury-mercurous chloride or silver-silver chloride electrode. It should be understood that the use of these materials for the sensor electrode 20 and reference electrode 21 are exemplary only. Other electrode compositions for the sensor electrode 20 and reference electrode 21 are possible for measuring pH levels or other chemical characteristics.

Figure 2B:
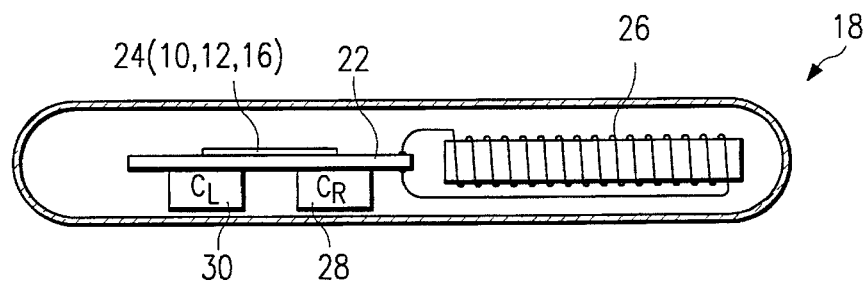
FIG. 2B illustrates another embodiment of a sensor, measurement circuit, and responder unit in a housing according to the teachings of the present invention.

The sensor 12, which is coupled to a PCB board 22, provides data to an integrated circuit 24. In the present invention, the integrated circuit 24 is comprised of the responder unit 16 and the measurement circuit 10. It should be understood that the combination of the responder unit 16 and measurement circuit 10 in a single integrated circuit is exemplary only. Other configurations may be used in which the responder unit 16 and measurement circuit 10 are separate. In addition, the responder unit 16 and measurement circuit 10 can further be combined with a sensor 12 in a single integrated circuit. FIG. 2B illustrates such an embodiment, wherein the sensor 12, measurement circuit 10, and responder unit 16 are combined in a single integrated circuit. As shown in FIG. 2B, no part of the sensor 12 extends outside of the housing 18. Such a sensor 12 may comprise, for example, a temperature sensor, among others. With these components completely contained within housing 18, electromagnetic noise is greatly reduced and significant corrosion immunity is obtained. For example, in hostile chemical environments, little chance for corrosion is presented, due to the protection from housing 18. Furthermore, with the components so close together, wiring is basically eliminated, and electromagnetic noise is greatly reduced. With the embodiment of FIG. 2B, in which the sensor 12 is completely contained within housing 18, there is no requirement that the sensor 12, measurement circuit 10, and responder unit 16 reside on a single integrated circuit.

The responder unit 16 is able to communicate with interrogation unit 14 through the use of radio frequency ("RF") waves. With this approach, wireless, contactless reading of the chemical sensor 12 may be accomplished. Such communication provides an important technical advantage of the present invention, since reading of the chemical sensor 12 may be performed conveniently and quickly. In addition, the wireless, contactless reading of the chemical sensors 12 eliminates or reduces noise problems in the chemical sensor system.

The reception of the RF interrogation signal at the responder unit 16 is performed by a parallel resonant circuit having a coil 26 and a capacitor 28. Connected to the parallel resonant circuit is a capacitor serving as an energy accumulator 30. The resonant circuit receives an interrogation signal and energy from that signal is stored in the energy accumulator 30. The energy stored from the signal is used to operate the measurement circuit 10 and responder unit 16.

In operation, the circuit in FIG. 2A may be used to measure chemical parameters such as pH. For pH measurement, a potential develops in relation to the hydrogen ion concentration at the sensor electrode 20. The potential difference is measured between the sensor electrode 20 and reference electrode 21. Measurement circuit 10 determines the system pH level based on the potential difference.

Figure 3:
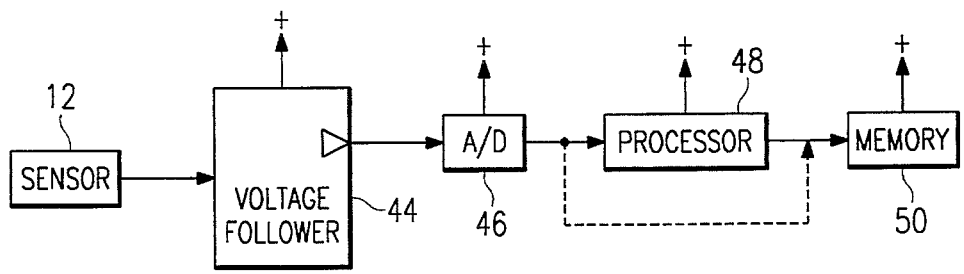
FIG. 3 illustrates a block diagram of an embodiment of a measurement circuit for reading a chemical sensor according to the teachings of the present invention.

FIG. 3 illustrates a block diagram of a particular embodiment of a measurement circuit 10 for reading the sensor 12.

In this particular embodiment, the measurement circuit is operable to measure potential differences at sensor 12. The measurement of potential differences is frequently used to determine chemical parameters such as pH levels. As shown in FIG. 3, data from sensor 12 are input to a voltage follower 44. Voltage follower 44 outputs a signal proportional to the potential difference measured at sensor 12. This output may be amplified. The output of voltage follower 44 is input to an analog-to-digital converter 46, which converts the signal to a digital signal. This digital signal is then read by a processor 48 and stored in memory 50. In addition, the output of analog-to-digital converter 46 may be stored directly to memory 50, as shown by the dashed line of FIG. 3.

As will be discussed below, an important technical advantage of the present invention is the fact that the measurement circuit may be powered by an interrogation signal sent by interrogation unit 14. Thus, the sensor 12 and measurement circuit 10 do not require a battery or other local power source. Because no battery is needed, the sensor 12 and associated circuits may be placed in an environment to be monitored and therefore, require little or no maintenance.

Figure 4:
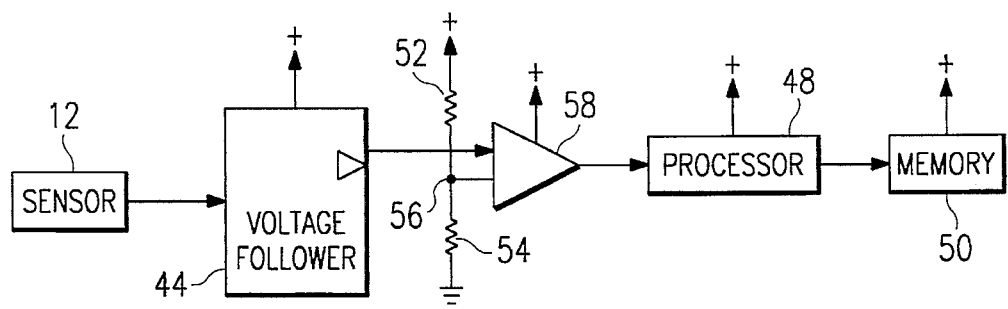
FIG. 4 is another embodiment of a measurement circuit for reading a chemical sensor according to the teachings of the present invention.

FIG. 4 illustrates another embodiment of a measurement circuit 10 for reading potential differences at chemical sensor 12 according to the teachings of the present invention. As shown in FIG. 4, voltage follower 44 outputs a signal that is proportional to the potential difference detected at chemical sensor 12. The output of voltage follower 44 is coupled to the input of a comparator 58. Comparator 58 compares the output voltage of voltage follower 44 with a reference voltage at node 56 generated by resistor dividers 52 and 54. Thus, the output of comparator 58 will be in one state if the output of voltage follower 44 is less than the voltage at node 56, and the output of comparator 58 will be in another state if the output of voltage follower 44 is greater than the voltage at node 56.

The voltage at node 56 may be set by analyzing the desired level of the predetermined characteristic of the chemical sensor. For example, the voltage level at node 56 may be set such that the state of comparator 58 changes when the output of the chemical sensor 12 reaches a certain set point. Processor 48 reads the output of comparator 58 and then stores information based on that output in memory 50.

The two embodiments of measurement circuits for reading chemical sensor 12 shown in FIG. 3 and FIG. 4 are exemplary only. It should be understood that other circuits may be used to read and record information from sensors 12 without departing from the intended scope of the present invention.

Figure 5:
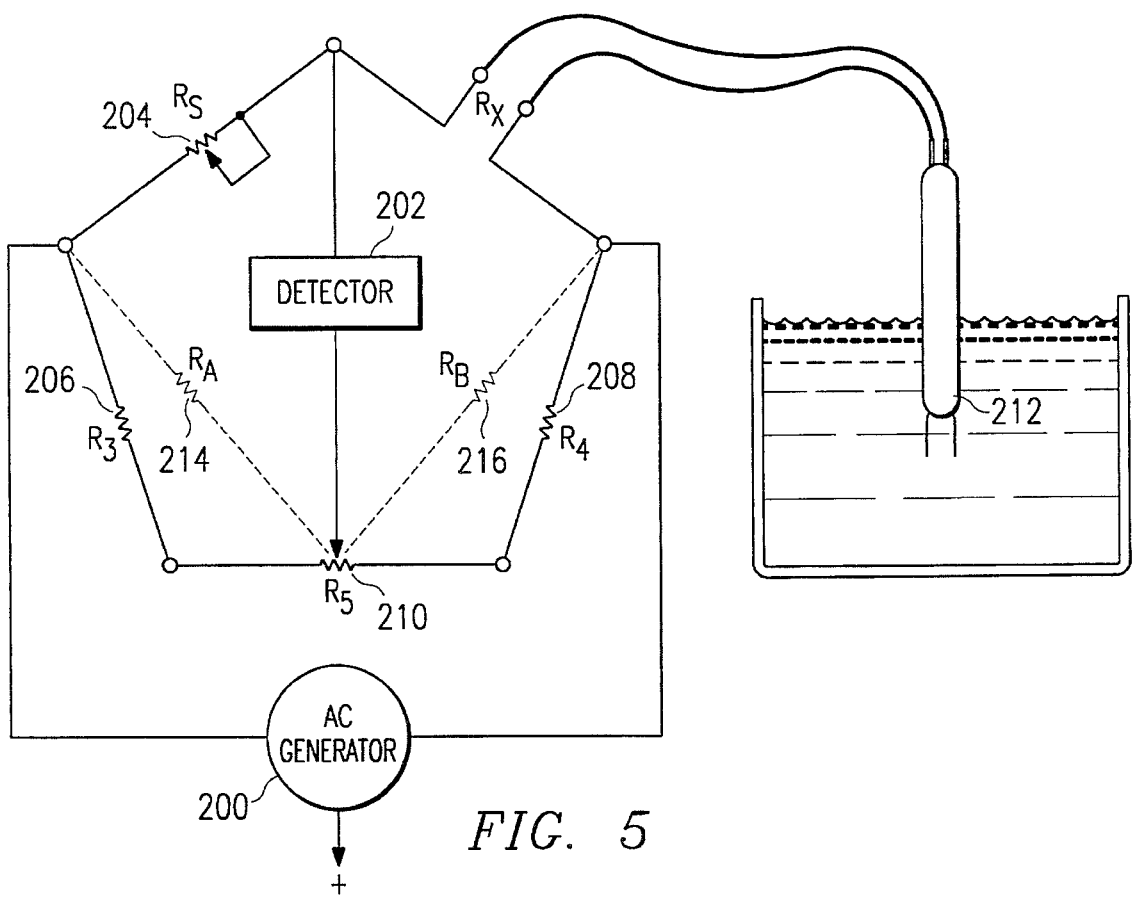
FIG. 5 is a diagram of an embodiment of a measurement circuit for measuring conductivity according to the teachings of the present invention.

For example, FIG. 5 illustrates an embodiment of a measuring circuit for measuring conductivity according to the present invention. As shown in FIG. 5, an alternating current Wheatstone bridge is used for measuring electrolytic resistivity (the reciprocal of conductivity). An AC generator 200 provides the Wheatstone bridge with a bridge voltage. The detector 202 is an AC voltage sensitive device that generates a signal proportional to the current flow through the device. The AC generator 200 may be powered by an interrogation signal sent by interrogation unit 14. In addition, it should be understood that other AC generators may be used. For example, the AC source may be a low-voltage tap on a line-frequency operated transformer, or a battery or line-powered electronic oscillator.

The Wheatstone bridge is comprised of a number of resistances. First, a variable standard arm resistance ($R_s$) 204 is provided to permit changing the range of the measurement circuit. Resistors 206 and 208 are end resistors that define the limits of bridge calibration. In addition, a calibrated slidwire potentiometer 210 is placed between resistors 206 and 208. The calibrated slidwire potentiometer 210 is in series with the detector 202, and thus variable values in the potentiometer 210 cause no error in bridge readings. The final resistance in the Wheatstone bridge is provided by the effective resistance ($R_x$) of the electrolyte between the electrodes of conductivity sensor 212.

In operation, the range of the meter is controlled by resistors 206 and 208. For example, if resistors 206 and 208 were short-circuited, then the current measurement range would be zero to infinity. Therefore, by increasing the resistance of resistors 206 and 208 as compared to potentiometer 210, the range is reduced. The resistors 206 and 208 and the potentiometer 210 create an effective resistance A ($R_A$) 214 and effective resistance B ($R_B$) 216. Balancing of the bridge circuit occurs when $R_A$ over the effective resistance $R_B$ equals the standard arm resistance 204 over the effective resistance of the electrolyte:

$$R_A/R_B = R_s/R_x$$

When the circuit is balanced, no current flows through the detector 202. However, current does flow through detector 202 when the bridge is not balanced. Therefore, the current detected can be used to determine the effective resistance of the electrolyte between the two electrodes of conductor sensor 212. From the effective resistance of the electrolyte, the conductivity can be determined by taking the reciprocal of the resistivity.

Figure 6:
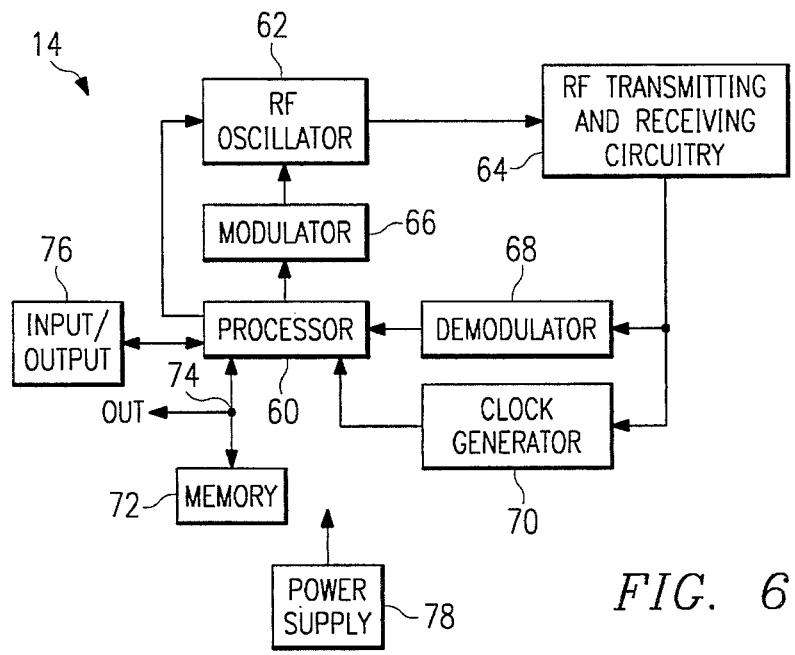
FIG. 6 is a block diagram of an interrogation unit according to the teachings of the present invention.

FIG. 6 illustrates a block diagram of interrogation unit 14 according to the teachings of the present invention. As shown in FIG. 6, a processor 60 controls RF oscillator 62. RF oscillator 62 generates an output that is coupled to RF transmitting and receiving circuitry 64. In a particular embodiment, RF oscillator 62 may operate at a nominal frequency of 125 kHz or 134.2 kHz. Processor 60 is also coupled to a modulator 66 which may be used to modulate the frequency (or amplitude or phase) of the output of RF oscillator 62. RF transmitting and receiving circuitry 64 is also coupled to demodulator 68 and clock generator 70. Demodulator 68 and clock generator 70 are coupled to processor 60. Processor 60 stores information received from demodulator 68 into memory 72.

Data from memory 72 or processor 60 may also be output to an external data acquisition system 18 through output 74. Similarly, data can be output to input/output device 76 as shown in FIG. 6. Input/output device 76 may also be used to initiate operation of the interrogation unit 14. Input/output device 76 may also comprise a display, on which information received from chemical sensor 12 may be displayed. A power supply 78 is provided for powering interrogation unit 14. Power supply 78 may be a rechargeable battery, non-rechargeable battery, or other power supply. In operation, interrogation unit 14 will be activated to read information from a remote chemical sensor 12. RF transmitting and receiving circuitry 64 transmits an interrogation signal. Sometime thereafter, transmitting and receiving circuitry 64 receives a response from responder unit 16. This response is input to clock generator 70 and demodulator 68. Clock generator 70 generates a clock based on the returned signal. Furthermore, demodulator circuit 68 demodulates the response. For example, the response may have been modulating using frequency-shift keying ("FSK"). Thus, a response at a particular frequency for a given amount of time will be recognized as a "0" and a receive signal at another frequency received from a given amount of time will be recognized as a "1." Processor 60 will read this data and store it to memory 72. In addition, the data may also be output at output 74 or to input/output device 76.

It may be desirable to individually address a plurality of chemical sensors 12 being used to monitor various chemical environments. With individual addressing, a single interrogation unit 14 permits a single data acquisition unit to be multiplexed to access multiple chemical sensors. The ability to access multiple chemical sensors with a single interrogation unit provides an important technical advantage of the present invention. The use of a single data acquisition unit to access multiple sensors prevents the inconvenience and other potential problems associated with detaching and reattaching data acquisition equipment to different sensors.

In an embodiment of the present invention, modulator 66 is provided to permit access to multiple sensors. In particular, the frequency (or amplitude or phase) of the output of the RF oscillator 62 is modulated by modulator 66, which is controlled by processor 60. In this way, an interrogation signal generated by RF transmitting and receiving circuitry 64 will be modulated according to the particular address of the particular chemical sensor 12 to be read. Thus, a chemical sensor 12 will respond to an interrogation signal only when the demodulated address corresponds to the predefined responder unit address. Upon detecting the proper responder unit address, the responder unit 16 transmits data from the measurement circuit 10 to the interrogation unit 14.

A particular embodiment of interrogation unit 14 is described in U.S. Pat. No. 5,053,774 entitled "*Transponder Arrangement*" and issued on Oct. 1, 1991. That patent is herein incorporated by reference.

Figure 7:
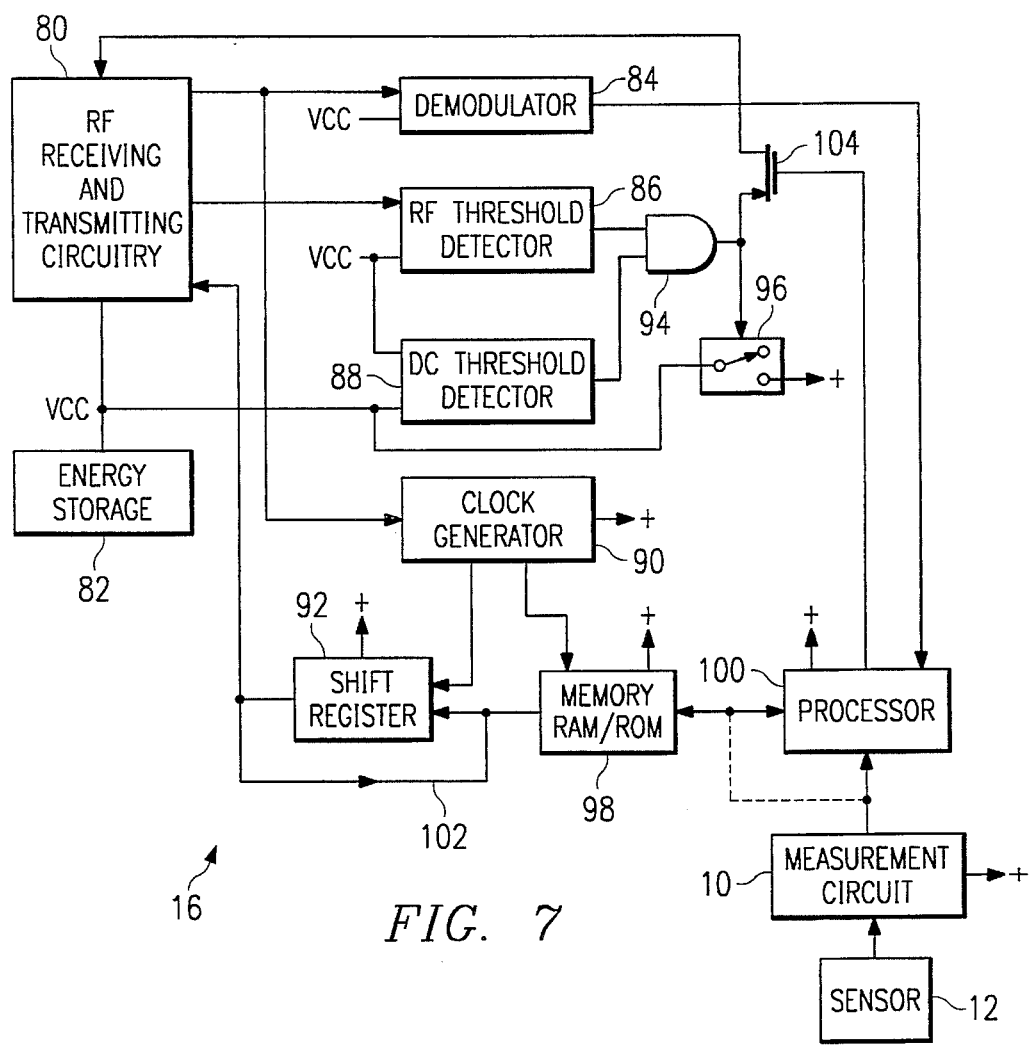
FIG. 7 is a block diagram of a responder unit according to the teachings of the present invention.

FIG. 7 illustrates a block diagram of a responder unit 16 according to the teachings of the present invention. As shown in FIG. 7, RF receiving and transmitting circuitry 80 is coupled to an energy storage 82, demodulator 84, RF threshold detector 86, DC threshold detector 88, clock generator 90, and shift register 92. The RF receiving and transmitting circuitry 80 is operable to receive and transmit data via RF frequencies between the interrogation unit 14 and the responder unit 16. RF threshold detector 86 and DC threshold detector 88 are coupled to an AND-Gate 94. The output of AND-Gate 94 controls a switch 96 which is used to couple power from energy storage 82 to clock generator 90 and shift register 92. The output of AND-Gate 94 is also coupled to circuitry 80 (as shown, through a switch 104 to be discussed, which is included for individual addressing). Also, the output of switch 96 is coupled to a memory 98, a processor 100, and measurement circuit 10. The memory 98 is coupled to processor 100, clock generator 90, and shift register 92. The processor 100 is also coupled to demodulator 84 and measurement circuit 10. Measurement circuit 10, as discussed above in connection with FIGS. 3–5, is used to read the output of chemical sensor 12 for processing and storage.

In operation, RF receiving and transmitting circuitry 80 receives an interrogation signal from interrogation unit 14. As a signal is received, energy is stored in energy storage 82, which may comprise a capacitor. At the end of the interrogation signal, RF threshold detector 86 will detect a decreased received RF energy, and will output a signal to AND-Gate 94. As discussed above, the received energy from the RF interrogation signal is stored in energy storage 82. Energy storage 82 will be used to power all of the circuitry within responder unit 16. Thus, no local battery or other power supply is needed for responder unit 16. This provides an important technical advantage, since a responder unit 16 will require less maintenance. Once the energy level within energy storage 82 reaches a level sufficient to power each of the devices within responder unit 16, DC threshold detector 88 will also output a signal to AND-Gate 94. Once the outputs from both detector 86 and detector 88 are received by AND-Gate 94, switch 96 will be activated, thus powering out the other circuitry on responder unit 16. Furthermore, it should be noted that the energy storage 82 may also be used to power measurement circuit 10.

The output of AND-Gate 94 is also coupled to RF receiving and transmitting circuitry 80 and triggers the transfer of energy from energy storage 82 through circuitry 80 to generate an RF carrier signal to be transmitted back to interrogation unit 14. This RF carrier signal is also used to generate clock signals through clock generator 90. Clock generator 90 controls shift register 92 and memory 98 such that data stored in memory 98 is transferred to shift register 92. The data output from shift register 92 is transmitted to RF receiving and transmitting circuitry 80. This output is used to modulate the RF carrier wave output by circuitry 80. For example, the bits output by shift register 92 may be used to cause FSK modulation of the RF carrier wave output by circuitry 80. Shift register 92 may also include a feedback loop 102. Feedback loop 102 will be used once all data to be transmitted are loaded within shift register 92. These bits will then be reloaded into the shift register as they are shifted out, so that the data to be transmitted to interrogation unit 14 may be retransmitted without needed to reaccess memory 98.

As discussed above, the measurement circuit 10 reads the output of sensor 12. Processor 100 loads the output of measurement circuit 10 into memory 98, or loads information in memory 98 based on the output of measurement circuit 10. Memory 98 may be a combination of random access memory, read-only memory, or EEPROM. The particular address of sensor 12 read by responder unit 16 may be included in the ROM or EEPROM portion of memory 98. The RAM portion of memory 98 will store the particular data generated by measurement circuit 10 and processor 100. Such address and sensor data will then be loaded from memory 98 to shift register 92. It should be noted, however, that address data need not be included in all applications of the present invention.

In addition, memory 98 may also be used as a calibration data storage memory. Processor 100 can read calibration data from memory 98 and provide calibration data for measurement circuit 10 and sensor 12. User memory 98 as shown in FIG. 7 to store calibration data is exemplary only. It should be understood that a separate memory may be used to store measurement calibration data or measurement circuit 10 and sensor 12 without departing from the intended scope of the present invention.

In addition, FIG. 7 illustrates the circuitry required to perform addressing of multiple chemical sensors. The demodulator circuit 84 demodulates signals from interrogation unit 14. The output of demodulator 84 is input to processor 100. Processor 100 compares the information demodulated by demodulator 84 with address data stored in memory 98. If the demodulated address from demodulator 84 corresponds to the address stored in memory 98, then the particular responder unit 16 and sensor 12 has been addressed and should respond. If the data does not match, then the particular responder unit has not been addressed, and will not respond. When individual addressing of responder unit 16 is desired, the output of AND-Gate 94 that is coupled to RF receiving and transmitting circuitry 70 will pass through a switch 104. Switch 104 is controlled by processor 100. Switch 104 will be closed only if the address received from interrogation unit 14 corresponds to the address of responder unit 16. With the switch 104 open, no response is enabled. Thus, the switch 104 and processor 100 operate as enabling circuitry. The enabling circuitry presents an important technical advantage of the present invention. Through the enabling circuitry and addressing capabilities, a single data acquisition unit and interrogation unit may operate to multiplex reception of data from multiple chemical sensors.

The processor 100 may be a programmable microprocessor. However, the use of a microprocessor is exemplary only. Other processing units may be used without departing from the intended scope of the present invention, including a microcontroller, a programmable array logic, gate array logic, or any other circuitry capable of performing logic and control functions discussed herein.

A particular embodiment for responder unit 16 is disclosed in U.S. Pat. No. 5,053,774, entitled *"Transponder Arrangement"* and issued on Oct. 1, 1991. That patent is herein incorporated by reference.

Although the present invention has been described in detail, it should be understood that various changes, substitutions, and alterations can be made without departing from the intended scope as defined by the appended claims.

What is claimed is:

1. A chemical sensor system, comprising:
   an interrogation unit operable to transmit an interrogation signal and receive responses;
   an environmentally-sealed housing;
   a responder unit disposed within said environmentally-sealed housing, said responder unit being powered from said interrogation signals, said responder unit operable to receive said interrogation signals and transmit responses to said interrogation signals;
   a chemical sensor disposed within said housing and operable to generate an output based on predetermined physical parameters;
   at least one electrode extending outwardly from said housing and in electrical communication with said chemical sensor; and
   a measurement circuit disposed within said housing and coupled to said chemical sensor, said measurement circuit operable to measure the output of said chemical sensor and provide measurement data to be communicated to said interrogation unit in said responses.

2. The system of claim 1, wherein said measurement circuit and said responder unit comprise a single integrated circuit.

3. The system of claim 1, wherein said chemical sensor, said measurement unit, and said responder unit comprise a single integrated circuit.

4. The system of claim 1, wherein said responder unit further comprises a calibration data storage memory operable to provide calibration data for said measurement circuit.

5. The system of claim 1, wherein said chemical sensor is operable to measure conductivity.

6. The system of claim 1, wherein said chemical sensor is operable to measure pH levels.

7. The system of claim 1, wherein said measurement circuit comprises:
   a voltage follower coupled to said chemical sensor;
   an analog to digital converter coupled to said voltage follower, said analog to digital converter operable to generate digital measurement data;
   a processor coupled to said analog to digital converter; and
   a memory coupled to said processor, such that said processor directs said digital measurement data to said memory.

8. The system of claim 1, wherein said measurement circuit comprises:
   a voltage follower coupled to said chemical sensor, said voltage follower generating a voltage based on said chemical sensor output;
   a comparator coupled to said voltage follower, said comparator having a first output state and a second output state, depending on the level of said chemical sensor output;
   a processor coupled to said comparator; and
   a memory coupled to said processor, said processor operable to store information related to the state of said comparator to said memory.

9. The system of claim 1, wherein said measurement circuit comprises:
   a Wheatstone bridge circuit coupled to said chemical sensor, said chemical sensor providing an effective chemical resistance to said Wheatstone bridge circuit;
   an AC generator coupled to said Wheatstone bridge circuit, said AC generator operable to provide a bridge voltage to said Wheatstone bridge circuit;
   a detector coupled to said Wheatstone bridge circuit, said detector operable to measure current flow in said Wheatstone bridge circuit.

10. A chemical sensor system, comprising:
    an interrogation unit operable to transmit an interrogation signal and receive responses;
    a plurality of environmentally-sealed housings;
    a plurality of chemical sensors each disposed within one of said housings and operable to generate an output based on predetermined physical parameters;
    at least one electrode extending outwardly from each of said housings and in electrical communication with one of said chemical sensors;
    a plurality of measurement circuits, one each of said measurement circuits associated with one each of said chemical sensors and disposed in one of said housings, said measurement circuits operable to measure the outputs of said chemical sensors and provide measurement data; and
    a plurality of responder units, one each of said responder units associated with one each of said chemical sensors and one each of said measurement circuits and disposed in one of said housings, said responder units being powered from said interrogation signals, said responder units operable to receive said interrogation signals and transmit responses to said interrogation signals that include measurement data.

11. The system of claim 10, wherein at least one of said measurement circuits and associated responder unit comprise a single integrated circuit.

12. The system of claim 10, wherein at least one of said chemical sensors and associated measurement circuit and responder unit, comprise a single integrated circuit.

13. The system of claim 10, wherein at least one of said responder units further comprises a calibration data storage memory operable to provide calibration data for said measurement circuit.

14. The system of claim 10, wherein said interrogation unit is operable to modulate said interrogation signal to provide individual responder unit addressing, and wherein each of said responder units comprises:

a demodulator operable to demodulate interrogation signals into addresses;

a processor coupled to said demodulator and operable to compare the demodulated addresses with a responder unit address; and enabling circuitry operable to enable said responder unit only when said demodulated address matches said responder unit address.

* * * * *